(12) United States Patent
Pepin et al.

(10) Patent No.: US 11,298,544 B2
(45) Date of Patent: Apr. 12, 2022

(54) NERVE STIMULATION SYSTEMS AND METHODS USING AN EXTERNAL WIRELESS POWER SOURCE

(71) Applicant: Galvani Bioelectronics Limited, Middlesex (GB)

(72) Inventors: Brian Marc Pepin, Mountain View, CA (US); Brian Otis, Mountain View, CA (US)

(73) Assignee: GALVANI BIOELECTRONICS LIMITED, Brentford (GB)

( * ) Notice: Subject to any disclaimer, the term of this patent is extended or adjusted under 35 U.S.C. 154(b) by 177 days.

(21) Appl. No.: 15/999,427

(22) PCT Filed: Feb. 17, 2017

(86) PCT No.: PCT/US2017/018371
§ 371 (c)(1),
(2) Date: Aug. 17, 2018

(87) PCT Pub. No.: WO2017/143191
PCT Pub. Date: Aug. 24, 2017

(65) Prior Publication Data
US 2020/0197699 A1 Jun. 25, 2020

Related U.S. Application Data

(60) Provisional application No. 62/296,273, filed on Feb. 17, 2016.

(51) Int. Cl.
*A61N 1/36* (2006.01)
*A61N 1/05* (2006.01)
(Continued)

(52) U.S. Cl.
CPC ......... *A61N 1/3614* (2017.08); *A61N 1/0556* (2013.01); *A61N 1/36139* (2013.01);
(Continued)

(58) Field of Classification Search
CPC ............ A61N 1/37229; A61N 1/37223; A61N 1/3787; A61N 1/36139; A61N 1/0556;
(Continued)

(56) References Cited

U.S. PATENT DOCUMENTS 6,175,767 B1 * 1/2001 Doyle, Sr. .......... A61N 1/36036
607/57
2005/0283203 A1 * 12/2005 Flaherty ............... A61B 5/6864
607/48
(Continued)

FOREIGN PATENT DOCUMENTS

WO WO-2015139053 A1 * 9/2015 ........... A61B 5/4836

OTHER PUBLICATIONS

International Patent Application No. PCT/US2017/018371; Int'l Written Opinion and the Search Report; dated Apr. 28, 2017; 16 pages.

*Primary Examiner* — Carl H Layno
*Assistant Examiner* — Anh-Khoa N Dinh
(74) *Attorney, Agent, or Firm* — BakerHostetler

(57) ABSTRACT

Systems and methods are provided for stimulating one or more nerves with an implantable device. The implantable device may comprise an antenna circuit including a loop antenna and a control circuit including a rectifying diode for rectifying an alternating voltage induced in the antenna circuit by an external electromagnetic field. The implantable device may also include a chargeable storage element for storing energy from the rectified voltage without using a battery. The device may also include an electrode array containing a set of electrodes for emitting an electric field using the stored energy in response to a control signal received from the control circuit. The components of the device may be affixed onto a soft polymer substrate including a linkable peripheral tab on at least two edges of a
(Continued)

substantially rectangular body section of the substrate for forming a cuff about the one or more nerves to be stimulated.

25 Claims, 5 Drawing Sheets

(51) Int. Cl.
<table>
<tr><td>A61N 1/372</td><td>(2006.01)</td></tr>
<tr><td>A61N 1/378</td><td>(2006.01)</td></tr>
<tr><td>H02J 50/10</td><td>(2016.01)</td></tr>
<tr><td>H02J 50/20</td><td>(2016.01)</td></tr>
<tr><td>H02J 50/40</td><td>(2016.01)</td></tr>
<tr><td>H02J 50/80</td><td>(2016.01)</td></tr>
<tr><td>H02J 7/02</td><td>(2016.01)</td></tr>
<tr><td>H02J 7/34</td><td>(2006.01)</td></tr>
</table>

(52) U.S. Cl.
CPC ..... *A61N 1/36178* (2013.01); *A61N 1/36192* (2013.01); *A61N 1/3787* (2013.01); *A61N 1/37229* (2013.01); *H02J 7/02* (2013.01); *H02J 7/345* (2013.01); *H02J 50/10* (2016.02); *H02J 50/20* (2016.02); *H02J 50/40* (2016.02); *H02J 50/80* (2016.02)

(58) Field of Classification Search
CPC .............. A61N 1/3614; A61N 1/36178; A61N 1/36192; A61N 1/3758; A61B 5/6877; A61B 5/4041; A61B 5/24; A61B 5/686; A61B 2560/0219; A61B 2562/0209; A61B 2562/164; H02J 50/20; H02J 50/80; H02J 50/10; H02J 50/40; H02J 7/02; H02J 7/345
See application file for complete search history.

(56) References Cited

U.S. PATENT DOCUMENTS

<table>
<tr><td>2010/0331933 A1</td><td>12/2010</td><td>Carbunaru et al.</td></tr>
<tr><td>2012/0123293 A1</td><td>5/2012</td><td>Shah et al.</td></tr>
<tr><td>2013/0018439 A1*</td><td>1/2013</td><td>Chow .................. A61N 1/3787<br>607/60</td></tr>
<tr><td>2013/0079843 A1</td><td>3/2013</td><td>Mashiach</td></tr>
<tr><td>2014/0031915 A1*</td><td>1/2014</td><td>Mashiach .......... A61N 1/36071<br>607/134</td></tr>
<tr><td>2014/0200626 A1*</td><td>7/2014</td><td>Campbell .......... A61N 1/36071<br>607/46</td></tr>
<tr><td>2014/0277258 A1*</td><td>9/2014</td><td>Mercanzini .......... A61B 5/6846<br>607/45</td></tr>
<tr><td>2015/0057720 A1*</td><td>2/2015</td><td>Ko ....................... A61N 1/3787<br>607/60</td></tr>
</table>

* cited by examiner

NERVE STIMULATION SYSTEMS AND METHODS USING AN EXTERNAL WIRELESS POWER SOURCE

CROSS REFERENCE TO RELATED APPLICATIONS

This application is a U.S. national application of International Application No. PCT/US17/18371, filed Feb. 17, 2017, which claims priority to U.S. Provisional Application No. 62/296,273, filed Feb. 17, 2016, which is incorporated herein by reference in the entirety.

TECHNICAL FIELD

The present disclosure generally relates to nerve stimulation systems and methods for individuals. More particularly, and without limitation, the disclosed embodiments relate to systems and methods for stimulating peripheral nerves with an implantable device using a wireless transmitter integrated into an external object.

BACKGROUND DESCRIPTION

Conventional commercial implants for nerve stimulation systems may use a battery as a power source. Batteries may be used due in part to the power levels required for adequate nerve stimulation, as well as the continuous, on-demand nature of the underlying therapies. Including a battery within an implant, however, complicates the design of the implant, makes them more cumbersome and costly. In addition, such arrangements may require more elaborate surgical procedures for implantation.

In view of the above and other factors, conventional implants for nerve stimulation systems suffer from numerous drawbacks. These drawbacks are especially acute in situations where a contemplated therapy (e.g., for certain chronic conditions such as rheumatoid arthritis, treatment-resistant depression, and inflammatory bowel disease) does not require large charge levels or on-demand power supply.

SUMMARY

The disclosed embodiments include systems and methods for stimulating a peripheral nerve with a batteryless, implantable device. In certain embodiments, the stimulation may have no therapeutic effect. For instance, the stimulation may be for the sole purpose of determining a plurality of pulse parameters, as discussed further below. The implantable device may comprise an antenna circuit tunable to a working frequency, the antenna circuit comprising a loop antenna. The implantable device may also comprise a control circuit coupled to the antenna circuit, the control circuit comprising a rectifying diode configured to rectify an alternating voltage induced in the antenna circuit by an external electromagnetic field.

In accordance with embodiments of the present disclosure, the implantable device may also comprise a chargeable storage element coupled to the control circuit configured to store energy from the rectified voltage, wherein the chargeable storage element does not include a battery. The implantable device may also comprise an electrode array coupled to the control circuit and the chargeable storage element, the electrode array containing a set of electrodes and configured to emit an electric field using the stored energy in response to a control signal emitted from the control circuit.

In addition, the implantable device may also comprise a soft polymer substrate configured to support the antenna circuit, the control circuit, the chargeable storage element, and the electrode array. The soft polymer substrate may comprise a rectangular body section and at least two peripheral tabs, the at least two peripheral tabs located on opposing edges of the body section and configured to adjoin such that the rectangular body section of the implantable device forms a cuff.

Furthermore, consistent with embodiments of the present disclosure, a wireless transmitter may be provided for generating the external electromagnetic field. The wireless transmitter may include an antenna array comprising a plurality of antennas having a different orientation. In addition, the wireless transmitter may be embedded in an external object configured to be worn in proximity to the implantable device.

In another aspect, the present disclosure is directed to a method for stimulating a nerve bundle with an implantable device. The implantable device may comprise an antenna circuit including one or more input terminals, a control circuit coupled to the antenna circuit, a chargeable storage element coupled to the control circuit, an electrode array coupled to the control circuit and chargeable storage element, and a plurality of sensors coupled to the control circuit. The method may comprise measuring, with the plurality of sensors, an electrical potential associated with the nerve bundle. The method may further comprise applying a modulated excitation signal from the control circuit to an input terminal of the antenna circuit, the excitation signal modulated based on the measured electrical potential. The method may also comprise demodulating a data signal formed in the antenna array from a first external electromagnetic field emitted from a wireless transmitter, the data signal including a plurality of pulse parameters indicative of characteristics of an electrical pulse. The method may further comprise applying a control signal to an electrode terminal of the electrode array, the control signal based on the plurality of pulse parameters. The method may also comprise emitting an electrical pulse from the electrode array in accordance with the plurality of pulse parameters to stimulate the nerve bundle, the electrical pulse generated from energy stored in the chargeable storage element.

In another aspect, the present disclosure is directed to a method for stimulating a nerve bundle with an implantable device. The implantable device may comprise an antenna circuit including one or more input terminals, a control circuit coupled to the antenna circuit, a chargeable storage element coupled to the control circuit, an electrode array coupled to the control circuit and capacitive storage, and a plurality of sensors coupled to the control circuit. The method may comprise rectifying a voltage induced in the antenna circuit from an external electromagnetic field with a rectifying diode in the control circuit and storing the rectified voltage as energy in the chargeable storage element. The method may also comprise applying a control signal from the control circuit to an electrode terminal of the electrode array in accordance with a plurality of pulse parameters. The method may further comprise emitting an electrical pulse from the electrode array using the stored energy to stimulate the nerve bundle, the electrical pulse based on the control signal and the plurality of pulse parameters.

In another aspect, the present disclosure is direct to a system for stimulating a nerve bundle with an implantable device. The implantable device may comprise an antenna circuit tunable to a working frequency, the antenna circuit comprising a loop antenna. The device may also comprise a control circuit coupled to the antenna circuit, the control circuit comprising a rectifying diode configured to rectify an alternating voltage induced in the antenna circuit by an external electromagnetic field. The device may further comprise a chargeable storage element, coupled to the control circuit, configured to store energy from the rectified voltage. The device may also comprise an electrode array coupled to the control circuit and the chargeable storage element, the electrode array comprising a set of electrodes and configured to emit an electric field using the stored energy in response to a control signal emitted from the control circuit. The device may further comprise a plurality of sensors coupled to the control circuit and a soft polymer substrate configured to support the antenna circuit, the control circuit, the chargeable storage element, and the electrode array, the soft polymer substrate comprising a rectangular body section and at least two peripheral tabs, the at least two peripheral tabs located on opposing edges of the body section and configured to adjoin such that the rectangular body section of the implantable device forms a cuff. The device may be configured to measure, with the plurality of sensors, an electrical potential associated with the nerve bundle. The device may be further configured to apply a modulated excitation signal from the control circuit to an input terminal of the antenna circuit, the excitation signal modulated based on the measured electrical potential. The device may also be configured to demodulate a data signal from a first external electromagnetic field emitted from a wireless transmitter, the data signal including a plurality of pulse parameters indicative of characteristics of an electrical pulse. The device may be further configured to apply a control signal to an electrode terminal of the electrode array, the control signal based on the plurality of pulse parameters. The device may also be configured to emit an electrical pulse from the electrode array in accordance with the plurality of pulse parameters to stimulate the nerve bundle, the electrical pulse generated from energy stored in the chargeable storage element.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION OF ILLUSTRATIVE EMBODIMENTS

Figure 1:
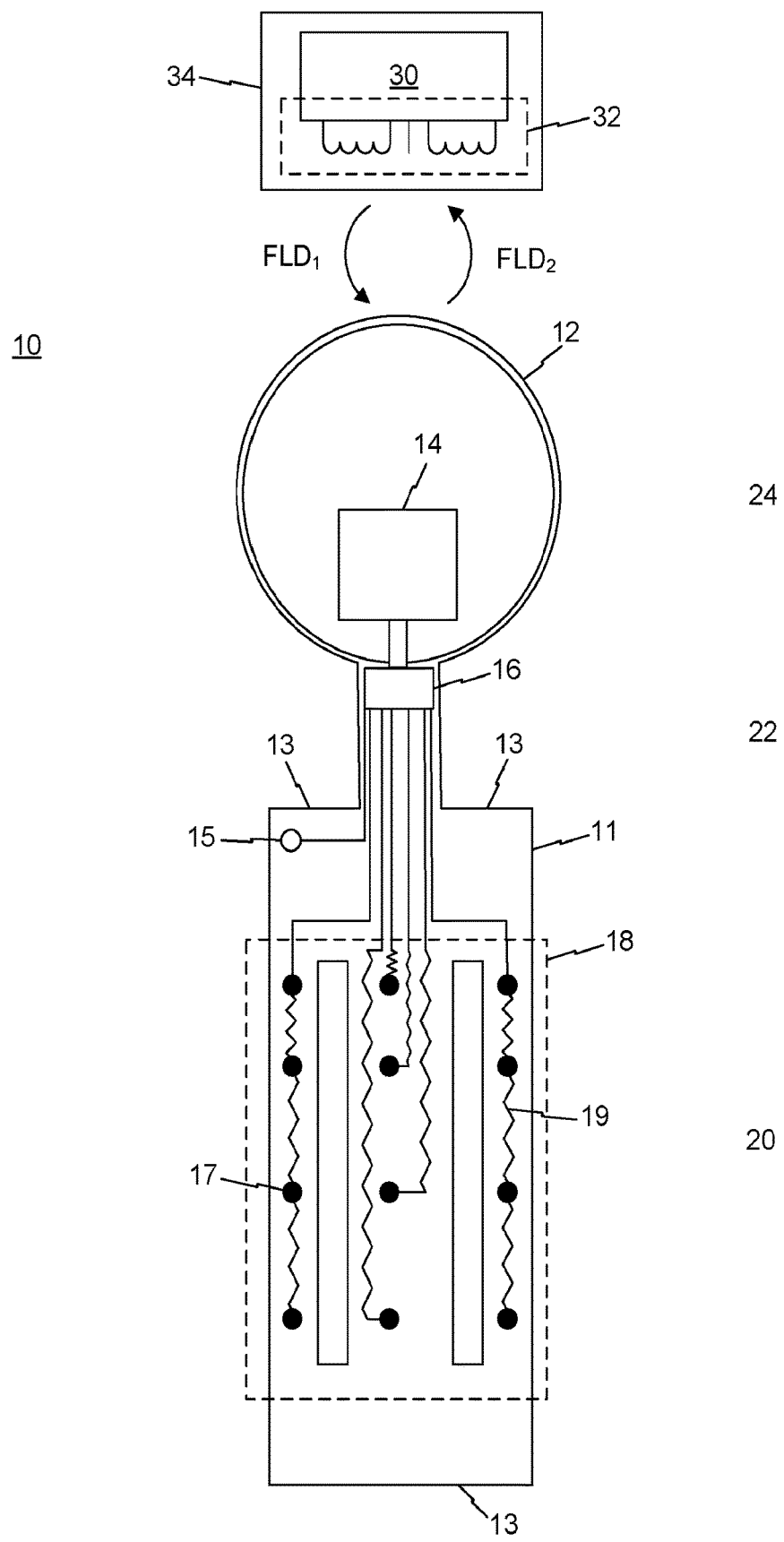
FIG. 1 depicts an example implantable device and wireless transmitter system, consistent with the disclosed embodiments.

The disclosed embodiments relate to systems and devices for stimulating a nerve, including for example, a peripheral nerve, with an implantable device that receives power from a wireless transmitter integrated into an external object. As a result, the implantable device may be batteryless and allow for implantation within an individual using a simple surgical procedure.

Stimulating a nerve as described herein may be defined as the delivery of electricity (e.g., electrical pulses) to a neuron, a nerve cell, a nerve bundle, or other target location of the nervous system (e.g., peripheral nervous system) intended to excite a neuron, a nerve cell, a nerve bundle, or other target location. The delivery of electricity may excite a nerve cell, for example, by inducing the flow of ions through the nerve cell membrane, which may trigger an action potential.

In some aspects, the implantable device receives power from a voltage induced within an antenna circuit using an external electromagnetic field emitted from a wireless transmitter. In some embodiments, the wireless transmitter may be embedded in an everyday object such as a scarf, neck pillow, tie, jewelry, or other similar object configured to be worn on the individual.

Consistent with embodiments of the present disclosure, the implantable device may include a capacitive storage or other chargeable storage elements in lieu of a battery for storing energy using induced voltage from an external object. This arrangement can thereby reduce the size and complexity of the implantable device.

As disclosed herein, the implantable device may include a control circuit for rectifying the induced voltage and/or applying a control signal to an electrode array of the implantable device for stimulating a nerve or nerve bundle in proximity to the implantable device.

In certain aspects, the components of the implantable device may be affixed to a single, soft, flexible polymer substrate. The substrate may include peripheral tabs along certain edges of the substrate so that, when sutured together, the implantable device forms a cuff around a nerve bundle.

A batteryless, flexible, implantable device consistent with embodiments disclosed herein may provide one or more technical improvements. For example, using a small capacitive storage in lieu of a battery may greatly reduce the complexity, size, and/or cost of the implant. In addition, the disclosed embodiments may facilitate minimizing implant size and/or surface area. These types of devices may reduce the complexity of the surgical procedures used for implantation by requiring only a single incision. Moreover, the disclosed embodiments may facilitate providing focused, targeted pulses of electricity for stimulating a nerve or other tissue based on certain time, tissue, and/or nerve parameters. In some aspects, these pulses may enable efficient delivery of electrical charge for short durations of time (e.g., lasting one to five minutes) and/or are predetermined times of the day.

Reference will now be made in detail to embodiments of the present disclosure, examples of which are illustrated in the accompanying drawings. Where possible, the same reference numbers will be used throughout the drawings to refer to the same or like parts.

FIG. 1 depicts an example system including an implantable device 10 and a wireless transmitter 30 for stimulating a nerve (e.g., peripheral) or portion thereof (e.g., nerve bundle) consistent with the disclosed embodiments. In some aspects, implantable device 10 may stimulate a nerve using energy generated from a voltage induced in an antenna of the implantable device by the external wireless transmitter.

Implantable device 10 may be also be configured to emit electromagnetic fields to the wireless transmitter to transmit data. In some embodiments, this data may be stored locally on implantable device 10, transmitted, decoded, and/or stored by the wireless transmitter (e.g., by demodulating a signal induced in an antenna within the wireless transmitter), or both. The stored data may comprise any information consistent with the disclosed embodiments, such as one or more potentials associated with a nerve or nerve bundle, information associated with electrical pulses emitted by implantable device 10 to stimulate a nerve (e.g., the amplitude, timing, duration, pulse width, etc.), or other such information. These embodiments, among others, are described in greater detail below.

In some aspects, implantable device 10 includes an antenna circuit 12 comprising one or more antennas for receiving and transmitting electromagnetic fields. Each of the one or more antennas may be any type of suitable antenna for this purpose, such as a coil antenna, loop antenna, dipole antenna, etc., and may be fitted with other components and parabolic reflectors, horns, passive radiators, or other such hardware for improving signal reception or transmission. Preferably, the antenna circuit 12 of implantable device 10 includes a loop antenna, as depicted in the example implantable device of FIG. 1. In certain aspects, one or more of the antennas within antenna circuit 12 may be flexible to facilitate implantation into a human subject.

In some embodiments, implantable device 10 may include separate antennas within antenna circuit 12 for transmitting and receiving electromagnetic fields, although such differentiation is not required. For example, implantable device 10 may include a single loop antenna to receive and/or transmit electromagnetic fields. As described in greater detail below, these electromagnetic fields may induce voltages within the antenna circuit 12 for subsequent processing in implantable device 10 (e.g., to store energy or data) or induce voltages in external systems (e.g., wireless transmitter 30) for energy or data storage. The antenna circuit 12 may be coupled to one or more components of implantable device 10 to facilitate processes consistent with the disclosed embodiments.

In some aspects, each of the antennas in the antenna circuit 12, or the antenna circuit as a whole, may be substantially tuned to a working frequency. In this context, an antenna circuit 12 may be substantially tuned to a working frequency in a temporal and/or physical sense. For example, an antenna circuit 12 may be substantially tuned to a working frequency when it is tuned to that frequency for a substantial period of time (e.g., greater than 30% of the time) and/or during periods of electromagnetic field reception or emission. In another example, the antenna circuit 12 may be substantially tuned to a working frequency when it is tuned to within some range of the working frequency, either on an absolute scale (e.g., a few MHz), or a relative scale (e.g., 15% in either direction from the working frequency). The antenna circuit 12 may be substantially tuned to a single, several, or variable working frequencies in this manner. In certain aspects, the one or more working frequencies of antenna circuit 12 may be dictated by the electrical properties of the internal circuitry of the antenna circuit, such as the values of the capacitors, resistors, internal resistances of the nested components, the presence of switches, etc., and the tuning of the antenna circuit for this purpose is within the skill of a skilled artisan. In some embodiments, for example, the antenna circuit 12 may be substantially tuned to a working frequency in the radio frequency range (e.g., approximately 3 kHz to 300 GHz, some narrower band therein, etc.). The working frequency may be predetermined, variable, and/or may be based on a particular transmission standard, such as those described by various ISO/IEC standards.

Implantable device 10 may include one or more control circuits 16 for controlling the operations of the device. In some aspects, control circuit 16 may include an ASIC (application specific integrated circuit) comprising one or more processers, memories (e.g., ROM, RAM, EEPROM, flash memory, etc.), or other components such as those described in connection with FIG. 5. Control circuit 16 may use these computing components to conduct processes consistent with the disclosed embodiments. For example, control circuit 16 may control the operations of implantable device 10 by using signals applied to other components of implantable device 10 (e.g., the antenna circuit 12, electrodes, etc.) to which control circuit 16 is coupled.

Control circuit 16 may include other types of hardware components in addition to its computing components. In one example, the control circuit 16 may include one or more rectifying diodes for rectifying an alternating voltage induced in the antenna circuit 12 (e.g., by an external magnetic field FLD1 generated from wireless transmitter 30) to transform it into a stable DC voltage for energy storage. Additionally or alternatively, the implantable device 10 may include one or more rectifying diodes elsewhere in the implant (e.g., within the antenna circuit 12, another component, etc.) to rectify this induced alternating voltage.

The control circuit 16 may be coupled to one or more components of implantable device 10, such as the antenna circuit 12, or other such components as described below. For example, in one aspect, control circuit 16 may be coupled to the antenna circuit 12 through one or more input terminals of the antenna circuit. Control circuit 16 may be configured to apply signals to the antenna circuit 12 through these input terminals to conduct processes consistent with the disclosed embodiments. In one example, control circuit 16 may be configured to apply an excitation signal to one or more of the input terminals of antenna circuit 12 so that the antenna circuit generates and/or emits an electromagnetic field FLD2 (e.g., oscillating at a particular working frequency) to transmit data or energy to another device (e.g., wireless transmitter 30).

Examples of such processes are described in further detail below. In addition, control circuit 16 may be coupled to the antenna circuit 12 for other purposes, such as to pull off and rectify a voltage induced in the antenna circuit by an external electromagnetic field FLD1. This coupling may occur through one or more of the input terminals and/or through a separate coupling that does not pass through the input terminals (e.g., so as to maximize the energy pulled off from the induced voltage, such as a point of higher impedance than the input terminals in the antenna circuit 12).

Implantable device 10 may include one or more chargeable storage elements 14 for storing electrical energy. The chargeable storage elements may reflect any type of component or device configured to store energy using electrical charges. In some aspects, for instance, the chargeable storage elements may comprise one or more capacitive storage elements 14. Capacitive storage elements may include any type of capacitor or capacitive component for storing electrical energy via electrical plates separated by a dielectric material (e.g., glass, ceramic, plastic, air, vacuum, paper, mica, oxide layer, etc.). In addition, in some embodiments, chargeable storage elements 14 does not reflect or include a battery. Thus, in some aspects, implantable device 10 does not include a battery in any of its components, rendering it a batteryless device. Additionally or alternatively, in some embodiments, the chargeable storage elements may include other types of chargeable storage elements or components for storing energy, such as button and coin cells, small chargeable batteries or fuel cells, lithium ion batteries, nanobatteries, etc.

In certain aspects, chargeable storage element(s) 14 may be configured to store relatively small amounts of electrical charge. For example, in some aspects, capacitive storage element 14 may have a capacitance of less than 1 nF or 75 pF. Preferably, capacitive storage element 14 may have a capacitance of about 50 pF (e.g., between 45 and 55 pF). These small capacitances may enable implantable device 10 to be configured to deliver relatively small or short pulses of electrical energy for particularized nerve treatment modalities that do not require the larger charge levels associated with batteries. For example, emerging therapies for chronic conditions such as rheumatoid arthritis, treatment-resistant depression, and inflammatory bowel disease may involve relatively lower charge injections that take place over short periods of time (e.g., 1-5 minutes) and/or at specific times of the day. In addition, these small capacitances may reduce the size and weight of implantable device 10, thereby simplifying the surgical procedures needed to implant the device and reducing its cost of manufacture.

Capacitive storage and/or other chargeable storage elements 14 generally may be coupled to one or more components of implantable device 10, such as control circuit 16, antenna circuit 12, etc. In one embodiment, for example, capacitive storage element 14 may be coupled to control circuit 16 via one or more rectifying diodes (e.g., diodes within or external to the control circuit) rectifying an alternating voltage induced in antenna circuit 12. In one example, capacitive storage 14 may be configured to store energy using an induced voltage in antenna circuit 12 that control circuit 16 has rectified. In another example, capacitive storage 14 may be coupled to the antenna circuit 12 directly (e.g., via one or more rectifying components such as a rectifying diode). Capacitive storage and/or other chargeable storage elements 14 may also be coupled to other components of implantable device 10 in a manner consistent with the disclosed embodiments.

In some aspects, implantable device 10 may include one or more electrode arrays 18, each comprising one or more sets of electrodes. In some aspects, each electrode array 18 may be configured to emit electrical fields to stimulate a nerve proximate to the implantable device 10. Each set of electrodes within electrode array 18 may include one or more electrodes 17 for this purpose. In some aspects, each electrode 17 may reflect a micro-electrode designed for maximum charge injection for stimulating a nerve.

Each electrode 17 within an electrode array 18 (or a subset of such electrodes, etc.) may be coupled to one another via a high-density, flexible interconnection 19 made substantially out of conductive material. In some embodiments, for example, interconnection 19 may be comprised substantially (e.g., 90 or 95 percent by weight) out of metals such as platinum or titanium. Other metals, suet, as gold, may also be used for interconnection 19. As depicted in FIG. 1, the electrodes 17 within electrode array 18 may be connected via interconnection 19 in series and/or parallel to provide multiple channels for increased selectivity of the parameters of the emitted electric field (e.g., magnitude, direction, location, etc.). In some aspects, this arrangement may provide for more targeted and efficient stimulation of a nerve.

The electrode array 18, its component set of electrodes, and/or individual electrodes 17 within the array may be coupled to one or more other components of implantable device 10 for conducting processes consistent with the disclosed embodiments. These couplings may occur through interconnection 19, couplings made from the same or similar materials, or other couplings electrically linking the coupled components. In some aspects, for instance, the electrode array 18 and/or its component sets of electrodes or individual electrodes 17 may be coupled to the control circuit 16, capacitive storage and/or other chargeable storage elements 14, and/or the antenna circuit 12 to conduct certain process disclosed herein. For example, electrode array 18 and/or any of its component electrodes 17 may be configured to emit an electric field to stimulate a proximate nerve in response to a control signal received from the control circuit 16 by using energy stored within capacitive storage 14 based on a voltage induced in antenna circuit 12 from an external electromagnetic field FLD1 and subsequently rectified (e.g., via a rectifying diode within control circuit 16). As depicted in the example implantable device of FIG. 1, each set of electrodes within electrode array 18 may be coupled to the control circuit 16 or capacitive storage 14 through a single electrode terminal or through several electrode terminals (e.g., wherein each electrode 17 in the set of electrodes is coupled to the control circuit directly).

Implantable device 10 may include one or more sensors 15 to conduct processes consistent with the disclosed embodiments. In certain aspects, the set of sensors 15 may include any sensor for measuring a physical or temporal parameter associated with implantable device 10 and/or its surroundings. For example, in one embodiment, the set of sensors 15 may include sensors for measuring the electrical potential between two points for conducting processes consistent with the disclosed embodiments, such as those described in connection with FIGS. 1-2. In addition, the set of sensors may include other sensors for measuring other characteristics such as pressure, temperature, time, resistance, conductance, electrical/magnetic flux, and so forth. Each sensor in the set of sensors 15 may be coupled to any other component of implantable device 10, such as control circuit 16, electrode array 18, capacitive storage and/or other chargeable storage elements 14, antenna circuit 12, etc.

Each of the components of implantable device 10 (e.g., the antenna circuit 12, capacitive storage and/or other chargeable storage elements 14, control circuit 16, set of sensors 15, etc.) may be affixed onto a soft polymer substrate 11 so that the substrate supports the affixed components. In certain embodiments, the substrate 11 may comprise a single piece of flexible material, such as silicone, to facilitate implantation into a patient and manipulation therein. In some aspects, the substrate 11 may comprise a plurality of sections to minimize the effective surface area and/or volume of the implantable device 10. Reducing the effective surface area, volume, and/or size of the implantable device 10 may further simplify the surgical procedures required to implant and/or manipulate the device, in addition to reducing its effective cost.

For example, in one aspect, the implantable device 10 may have a head section 24 of substrate 11 on which one or more components of the device are supported. As depicted in FIG. 1, for instance, the head section 24 may include the antenna circuit 12. In some embodiments, such as those when antenna circuit 12 includes a loop antenna, the head section 24 of substrate 11 may be substantially circular or elliptical in shape to accommodate antenna circuit without adding unnecessary surface area to the substrate. In certain aspects, head section 24 may be substantially circular (e.g., as depicted in the example implantable device 10 of FIG. 1) and/or has an effective eccentricity of less than 0.5 or 1. Head section 24 of substrate 11 may also structurally support other components of implantable device 10, such as capacitive storage and/or other chargeable storage elements 14. For example, as shown in FIG. 1, capacitive storage 14 may be affixed to the head section 24 of the substrate 11 inside the antenna circuit 12 (e.g., within a loop antenna) to further minimize the effective surface area of substrate 11. In this example, capacitive storage element or other chargeable storage element 14 may be coupled to control circuit 16 so as to receive a rectified voltage from control circuit 16 without going through the input terminals of antenna circuit 12 (e.g., to ensure the capacitive storage does not receive an alternating voltage). In other aspects, capacitive storage element or other chargeable storage element 14 may be embedded elsewhere on implantable device 10, such as within control circuit 16. In certain aspects, head section 24 of substrate 11 may take any shape substantially similar to that of a cross-section of the antenna circuit (e.g., substantially rectangular to accommodate a coil antenna, etc.).

Substrate 11 may also include a neck section 22 on which one or more components of implantable device 10 are affixed. In some aspects, for example, neck section 22 may structurally support control circuit 16 (which may include other components such as capacitive storage and/or other chargeable storage elements 14, other ASIC components, etc.). Neck section 22 may also support other components such as one or more input terminals of antenna circuit 12, one or more rectifying diodes for rectifying an alternating voltage induced in the antenna circuit from an external electromagnetic field FLD1 (e.g., within or separate from control circuit 16), or other components disclosed herein. Like head section 24, neck section 22 may take a shape so as to minimize the effective surface area of the neck section and/or implantable device 10. In the example implantable device depicted in FIG. 1, for instance, neck section 22 may have a substantially rectangular form on which the control circuit 16 is affixed. In certain aspects, a section of substrate 11 may be substantially rectangular when includes a pair of edges spanning a majority of the section that are substantially parallel (e.g., parallel to within a few degrees, such as 10 degrees). In other embodiments, neck section 22 may take other forms, such as that of a trapezoid, ellipse, etc. To further reduce the effective surface area of substrate 11, neck section 22 may have an average or maximal width smaller (e.g., narrower) than that of head section 24 or other sections of the substrate (e.g., a body section 20 described below).

Substrate 11 may include a body section 20 on which one or more components of implantable device 10 are affixed. For example, body section 20 of substrate 11 may structurally support one or more electrode arrays 18, any component electrode 17 thereof, a set of sensors 15, or any other component disclosed herein (e.g., one or more peripheral tabs as described in below). In some aspects, body section 20 may have a substantially rectangular form (e.g., in a similar manner to that of neck section 22) to minimize the effective surface area of implantable device 10. In the example implantable device depicted in FIG. 1, for instance, body section 20 may have a substantially rectangular extent over which the electrodes 17 of electrode array 18 span lengthwise and coupled though interconnections 19.

In some embodiments, one or more of the edges of body section 20 may include a set of peripheral tabs 13. In certain aspects, a peripheral tab 13 may comprise a region of implantable device 10 containing crenellations, ridges, grooves, adhesive material, etc., or other such region configured to be sutured, sewn, banded, interlocked, interconnected, attached, adhered, or otherwise bonded together with another peripheral tab such that, when adjoined, two or more peripheral tabs adhere to one another. In some aspects, each edge, periphery, boundary, or region proximate to these regions of body section 20 may include peripheral tabs 13 so that opposing edges of the body section may be fastened/interlocked/adjoined together lengthwise and/or widthwise. In other aspects, body section 20 may include peripheral tabs 13 only on certain edges, such as one or more first edges adjacent to (e.g., connected to) neck section 22 and an opposing edge not adjacent to the first edge(s), such as an opposing edge on the terminal edge of body section 10, as depicted in FIG. 1.

Figure 2:
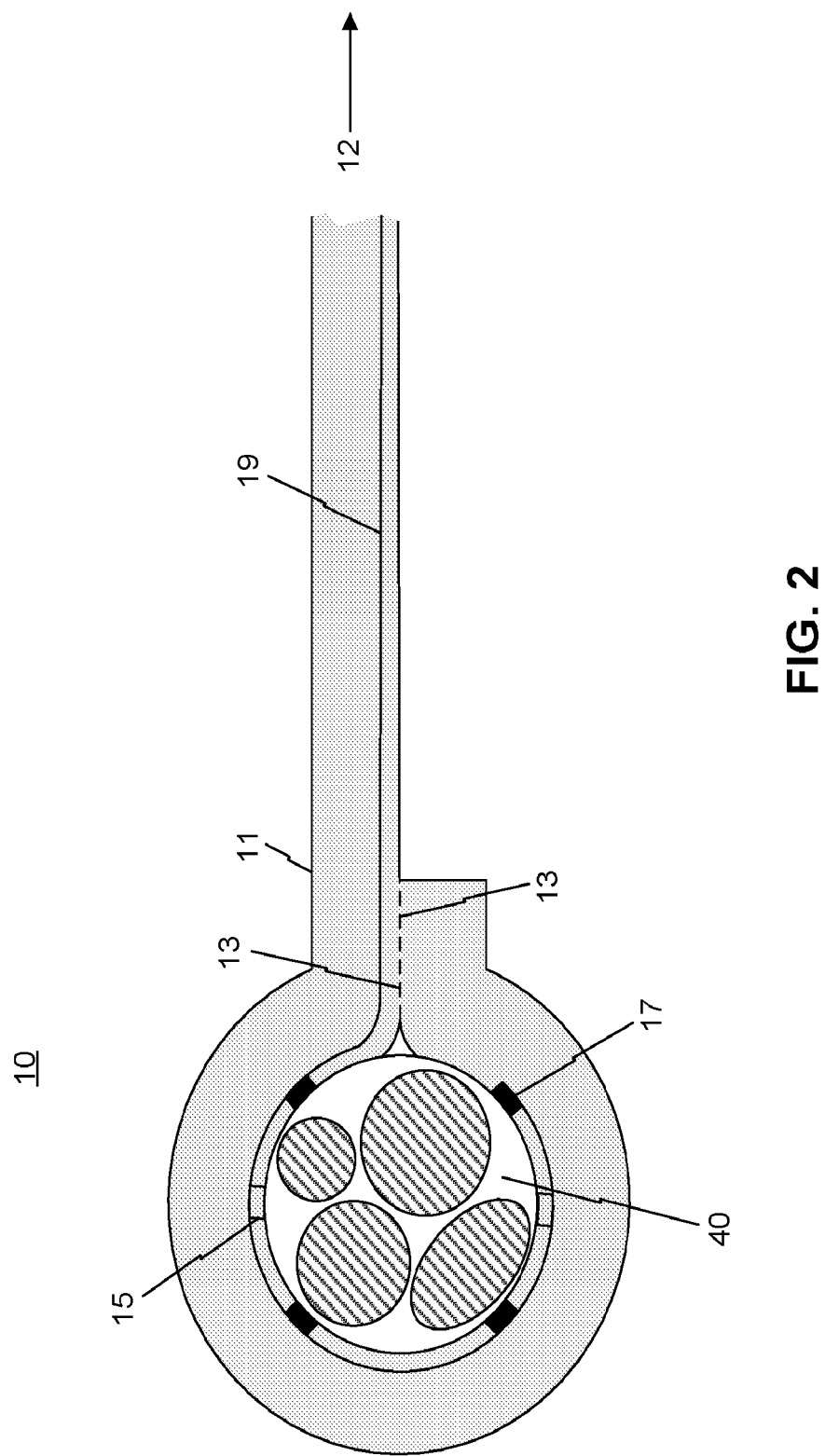
FIG. 2 depicts an example implantable device cuffed about a nerve bundle, consistent with the disclosed embodiments.

In some embodiments, two or more peripheral tabs 13 may be joined, adjoined, coupled, linked, sutured, interlocked, interconnected, or otherwise adhered together so that the body section 20 of substrate 11, and implantable device 10 generally, forms a cuff defining an interior region to the substrate 11. FIG. 2 depicts a cross-sectional view of an example implantable device 10 cuffed about a nerve bundle 40 within its interior region consistent with the disclosed embodiments. As shown in FIG. 2, two or more peripheral tabs 13 of opposing edges of implantable device 10 may be adjoined (denoted by the hashing along two separate peripheral tabs 13 of the implant) so that their resulting profile forms interacting, adhering, or locking connections within the regions wholly or partially comprising the peripheral tabs 13. When the peripheral tabs 13 are interconnected in this manner, an interior region forms within the body section 20 of the substrate with which implantable device 10 may interact.

In the example embodiment depicted in FIG. 2, for instance, peripheral tabs 13 of implantable device 10 have been joined together about a nerve bundle 40 so that implantable device 10 forms a cuff about the nerve bundle. The resulting cuff may facilitate stimulating the nerve bundle 40 with electrodes 17 of implantable device 10. The nerve bundle 40 may reflect one or more nerves or sets of nerves requiring electrical stimulation from implantable device 10. As depicted in FIG. 2, the electrodes 17 may be electrically coupled to one another and other components of implantable device 10 (e.g., control circuit 16, antenna circuit 12, etc.), via high-density, flexible interconnections 19. Forming a cuff with implantable device 10 about a nerve bundle 40 may facilitate targeted stimulation with electrical fields with minimal charge requirements and more efficient electric field emission. In addition, implantable device 10 may include sensors 15 within body section 20 so that the device may measure physical characteristics of the nerve bundle 40 within the formed cuff, such as electrical potential across the nerve bundle or cuff, etc. These measurements may be used for processes consistent with the disclosed embodiments.

Returning to FIG. 1, systems consistent with the disclosed embodiments may also include a wireless transmitter 30 for transmitting and receiving information and energy to and from implantable device 10. In some aspects, wireless transmitter 30 may reflect a system external to implantable device 10 and the individual within whom the implantable device is implanted. Wireless transmitter 30 may be configured to transmit and/or receive information and energy to and from implantable device 10 using electromagnetic fields as disclosed herein.

In some embodiments, wireless transmitter 30 may include an antenna array 32 comprising one or more antennas. Each of the one or more antennas of antenna array 32 may be any type of antenna consistent with the disclosed embodiments, such as those described in connection with antenna circuit 12. In one example, for instance, antenna array 32 may include a plurality of coil and/or loop antennas for generating and/or receiving electromagnetic fields. Each of the antennas may be substantially tuned to a working frequency in a similar manner as antenna circuit 12. In some aspects, for example, antenna circuit 12 and antenna array 32 may operate under the same working frequency or frequencies.

In addition, each of, a subset of, or at least two of the antennas within antenna array 32 may have a different orientation. In the example array depicted in FIG. 1, for example, antenna array 32 may include two coil antennas oriented face-on and one antenna oriented edge-on (e.g., depicted by a thin line between the two distinct coil antennas). In other aspects, the antennas within antenna array 32 may have other orientations and degrees of tilt, and the embodiment depicted in FIG. 1 is provided for illustrative purposes only. In certain aspects, including a plurality of antennas with varying orientations within antenna array 32 may assist in maximizing, optimizing, or improving the energy and/or data transmission and reception to and from wireless transmitter 30 and implantable device 10. In some embodiments, such an arrangement may assist in overcoming certain limitations or considerations like specific absorption rate (SAR) limits.

Wireless transmitter 30 may also include one or more other components (not pictured) for conducting operations or processes consistent with the disclosed embodiments. In some aspects, for example, wireless transmitter 30 may include a control circuit similar to control circuit 16 of implantable device 10. Additionally or alternatively, wireless transmitter 30 may include one or more processors, memories, communications buses, other components described in connection with FIG. 5. For example, in one embodiment, wireless transmitter 30 may include a demodulation circuit for demodulating a data signal formed in the antenna array 32 based on an external magnetic field FLD2 emitted by the implantable device 10. Each of the components of wireless transmitter 30 (e.g., the antenna array 32, a control circuit, a demodulation circuit, rectifying diodes, etc.) may be coupled to one another directly or indirectly, and/or in a manner similar to that as disclosed in connection with implantable device 10.

In certain aspects, wireless transmitter 30 may be embedded into an external object 34, as shown in FIG. 1. External object 34 may be implemented as any type of object or device external to (e.g., not a physical component of) wireless transmitter 30. In some aspects, external object 34 may be implemented as an object for facilitating ease-of-use of implantable device 10 and/or improving signal reception and transmission between the wireless transmitter 30 and implantable device 10. For example, external object 34 may be configured to be worn by an individual inside whom implantable device 10 is implanted so that wireless transmitter 30 and implantable device 10 are proximate to one another. By way of illustration, external object 34 may comprise a scarf, tie, jewelry, neck pillow, collar, brace, sleeve, sock, etc., or any other type of similar object configured to be worn so that the wireless transmitter 30 sits in physical proximity to where implantable device 10 has been implanted. When worn, external device 10 may have a substantially circular cross-section for wrapping about a portion of an individual's body, such as a neck, arm, torso, leg, hand, etc.

Figure 3:
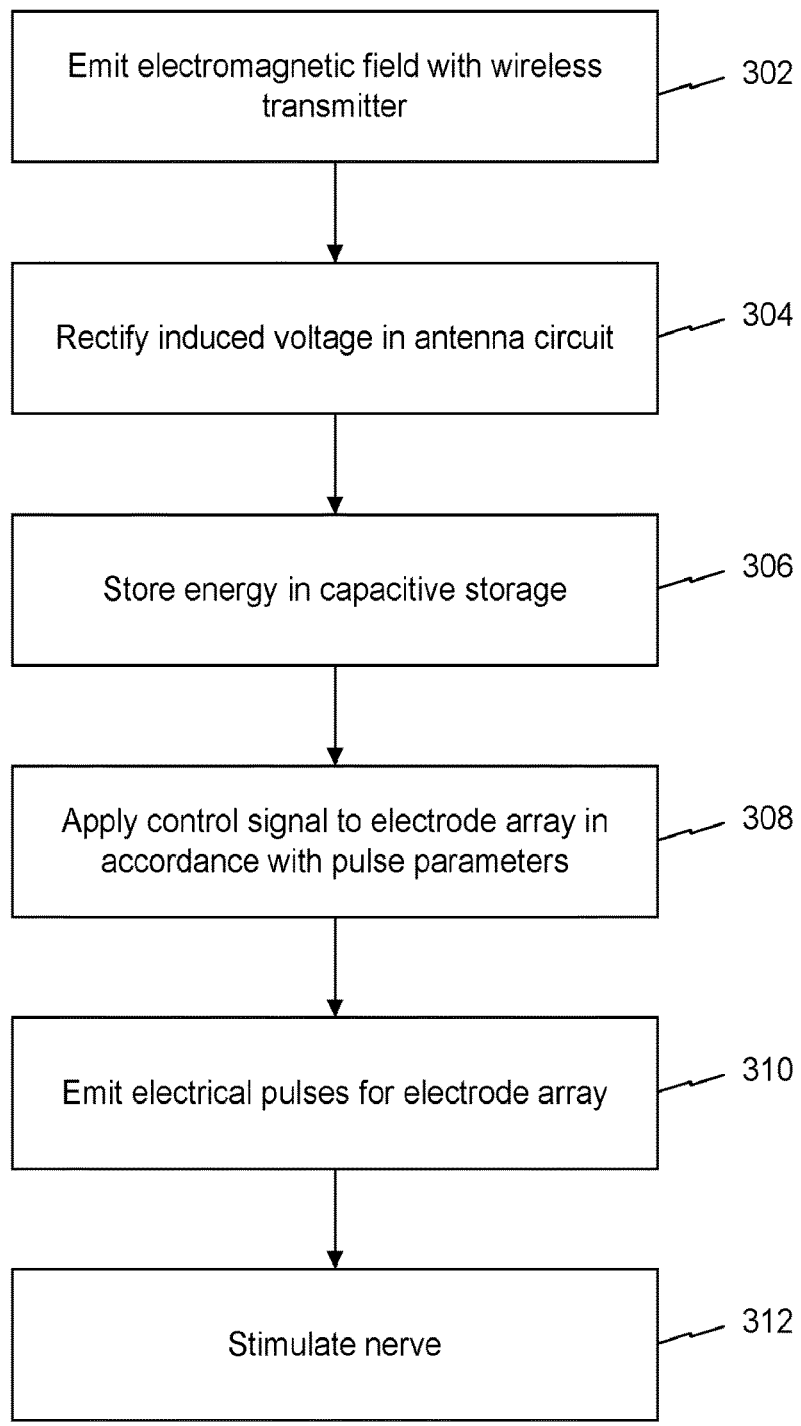
FIG. 3 depicts a flowchart of an example method for stimulating a nerve bundle, consistent with the disclosed embodiments.

Aspects consistent with the disclosed embodiments may enable implantable device 10 and wireless transmitter 30 to send and receive information and energy from one another to conduct operations and processes disclosed herein. For example, FIG. 3 depicts a flowchart of an example process 300 for stimulating a nerve or nerve bundle with implantable device 10 based on signals received from a wireless transmitter 30, consistent with the disclosed embodiments. In the example process 300 depicted in FIG. 3, implantable device 10 may be configured to stimulate a nerve bundle 40 using energy arising from an electromagnetic field FLD1 emitted from wireless transmitter 30 and stored in capacitive storage and/or other chargeable storage elements 14. In this example embodiment, wireless transmitter 30 may emit an electromagnetic field FLD1 using an excitation signal applied to antenna array 32 or antenna therein from a control circuit or other such controller in the wireless transmitter 30 (step 302). The external magnetic field FLD1 may induce an alternating voltage within the antenna circuit 12 of implantable device 10. Implantable device 10 may be configured to rectify this alternating voltage, such as through a rectifying diode within the antenna circuit 12 or control circuit 16 (step 304). For example, control circuit 16 may include at least one rectifying diode and may be coupled to the antenna circuit 12 and capacitive storage 14 such that the control circuit rectifies the alternating voltage from the antenna circuit 12 and stores the resulting DC voltage in the capacitive storage and/or other chargeable storage elements 14. In some aspects, implantable device 10 may use the rectified DC voltage to power operations of the device (e.g., the operations carried out by control circuit 16, electrode array 18, etc.) directly or indirectly by storing the resultant electrical energy in capacitive storage 14 and using the energy to power the implantable device (step 306).

When it is time to stimulate a nerve (e.g., based on a determination or signal consistent with the disclosed embodiments), control circuit 16 may apply a control signal to one or more electrode terminals of electrode array 18 and/or capacitive storage element or other chargeable storage element 14 such that the electrode array emits a pulse of electrical energy for stimulating the nerve (e.g., nerve bundle 40) using the energy stored in capacitive storage element or other chargeable storage element 14 (step 308). In some aspects, such as those described in connection with FIG. 2, implantable device 10 may form a cuff around the nerve bundle 40 using adjoining peripheral tabs 13 of the body section 20 of substrate 11 to facilitate targeted application of the electrical pulse with electrode array 18. In some embodiments, the control signal transmitted from control circuit 16 may be based on one or more pulse parameters reflecting characteristics of the electrical pulse required to stimulate a target nerve bundle 40, as described in further detail below.

In certain aspects, electrode array 18 may emit one or more pulses of electrical energy in this or similar ways to stimulate nerve bundle 40 (steps 310). In some embodiments, implantable device 10 may control the parameters of these pulses with control circuit 16, electrode array 18, and/or the control signal applied to the electrode array. The controlled pulse parameters may include the timing of the pulses (e.g., at what time of day the pulses are emitted), the duration of the pulses (e.g., one minute, five minutes, ten minutes, etc.), the amplitude or intensity of the pulses, the electrodes 17 used to generate the pulses (e.g., to specify a particular direction and/or orientation of the pulse), the waveform of the pulses (e.g., the width or wavelength of the pulses, the shape of the pulses, etc.), and/or any other parameter of the pulse consistent with the disclosed embodiments. Using these pulse parameters, implantable device 10 may stimulate a nerve bundle 40 with electrical pulse(s) emitted from electrode array 18 using energy stored in capacitive storage element or other chargeable storage element 14 deriving from an electromagnetic field FLD1 emitted from wireless transmitter 30.

Implantable device 10 and wireless transmitter 30 may be configured to send and receive data between each other using processes similar to that described above. For example, wireless transmitter 30 may be configured to transmit data (e.g., one or more pulse parameters) to implantable device 10 by modulating the amplitude of an excitation signal applied to antenna array 34 (e.g., from a control circuit within the wireless transmitter 30) in accordance with the data to be sent. This modulation may oscillate at one of the working frequencies of antenna array 32 and/or antenna circuit 12. The modulated signal may carry through the antenna array 34 to the emitted electromagnetic field FLD1 and may be detected as a data signal by antenna circuit 12 of implantable device 10. Implantable device 10 may contain a demodulation circuit coupled to the antenna circuit 12 to extract the modulated data signal and process and/or interpret the data. Additionally or alternatively, the demodulation circuit may be coupled to or integrated as a component within other components of implantable device 10 such as control circuit 16. The data transferred in this way may include any type of information consistent with the disclosed embodiments, such as information relating to pulse parameters of an electric pulse (e.g., timing, amplitude, duration, direction, etc.) to be generated with electrode array 18.

Implantable device 10 may be configured to transmit data to wireless transmitter 30 in a similar manner. For example, control circuit 16 of implantable device 10 may apply an excitation signal oscillating at a working frequency to an input terminal of antenna circuit 12 whose amplitude is modulated in accordance with the data being transferred (e.g., a measured electrical potential of nerve bundle 40). This modulated signal may form within antenna circuit 12 and carry through an electromagnetic field FLD2. Antenna array 32 of wireless transmitter 30 may detect the external magnetic field FLD2 produced by the modulated excitation signal. Wireless transmitter 30 may contain a demodulation circuit coupled to the antenna array 32 and/or other components of the transmitter (e.g., a control circuit) to demodulate the data signal formed in the antenna array 32 from the modulated excitation signal.

Figure 4:
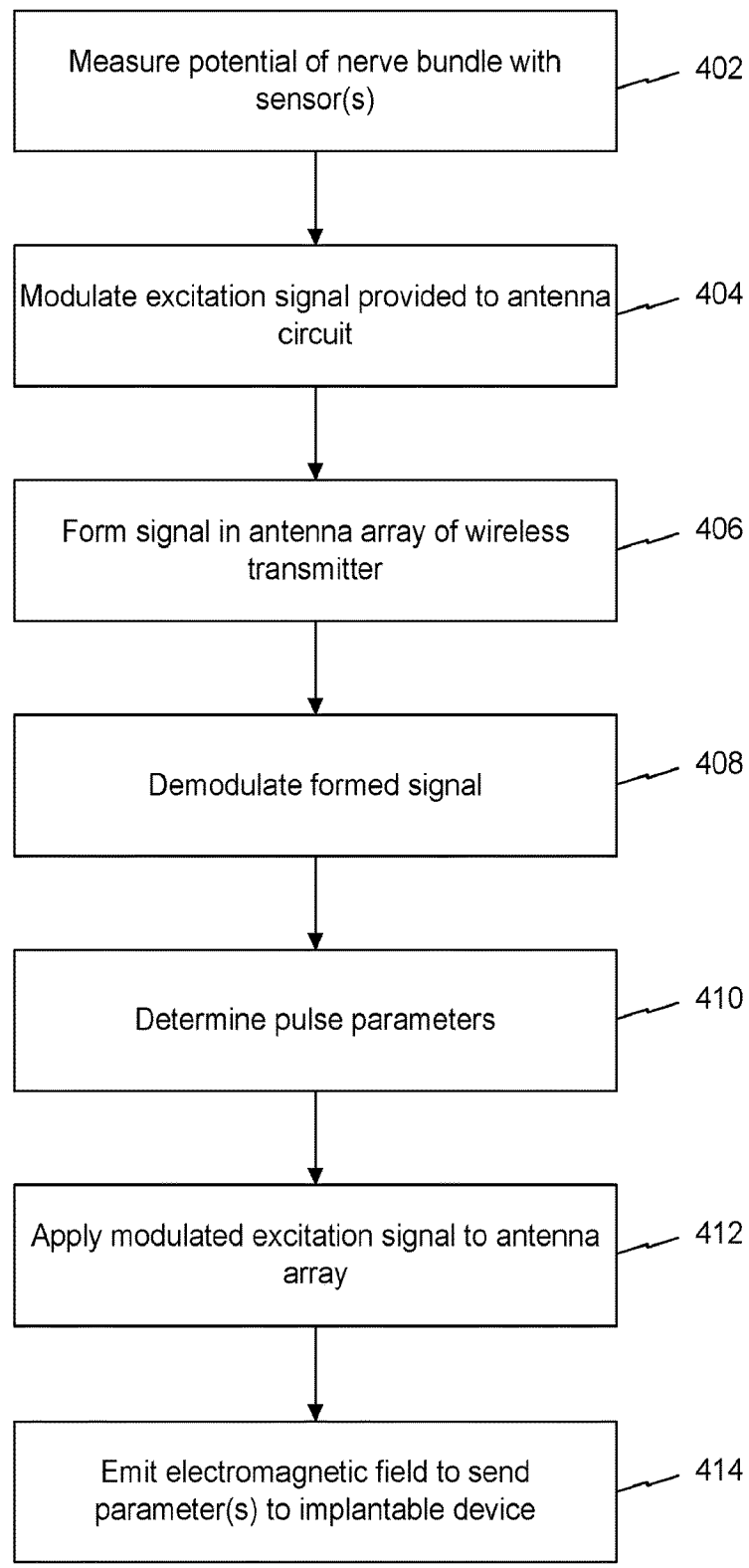
FIG. 4 depicts a flowchart of an example method for transferring data between an implantable device and a wireless transmitter, consistent with the disclosed embodiments.

By way of example, FIG. 4 depicts an example process 400 for transferring data between implantable device 10 and wireless transmitter 30 consistent with the disclosed embodiments. In some aspects of example process 400, implantable device 10 may measure the electrical potential of a nerve bundle 40 around which it has formed a cuff (e.g., as shown in FIG. 2) (step 402). Implantable device 10 may measure the electrical potential of nerve bundle 40 using a set of sensors 15 placed within a body portion 20 of flexible substrate 11. The sensors 15 may be coupled to control circuit 16 via interconnection 19 and may transmit the measured potentials to the control circuit for processing. The control circuit 16 may then send data containing the measured potentials to wireless transmitter 30 through antenna circuit 12 as described above. In one embodiment, for instance, control circuit 16 may modulate a first excitation signal applied to an input terminal of antenna circuit 12 (step 404), which transmits an electromagnetic field FLD2 that is received by antenna array 34. This electromagnetic field FLD2 generated from implantable device 10 may form a signal within the antenna array 34 of wireless transmitter 30 (step 406). In certain aspects, wireless transmitter may demodulate the formed signal in a demodulation circuit within wireless transmitter 30 to process and interpret the transmitted data {step 408). In other aspects, wireless transmitter may also include one or more antennas for receiving data separate from antenna array 34.

The data processing within wireless transmitter 30 may include, for instance, determining the status of nerve bundle 40 based on the measured electrical potentials (both historic and current) and computing one or more pulse parameters for implantable device 10 to use to stimulate the nerve bundle 40 (step 410). Wireless transmitter 30 may then send information associated with these pulse parameters to implantable device 10 to conduct processes consistent with the disclosed embodiments. For example, in one aspect, wireless transmitter may apply a second modulated excitation signal to one or more input terminals of its antenna array 32 or other antennas to send data to implantable device 10 (step 412). Implantable device 10 may receive the pulse parameter(s) from wireless transmitter 30 (e.g., using the processes described herein), store this information within memory of control circuit 16, and then apply a control signal to the electrode array 18 and/or a capacitive storage to stimulate the nerve bundle 40 in accordance with the received parameters (e.g., the timing, duration, strength, direction, etc. of the electric field) using the energy stored within the capacitive storage (step 414).

Implantable device 10 may also process information obtained via sensors 15 locally in addition to or in lieu of transmitting the measured data to wireless transmitter 30. For example, after measuring environmental data with sensors 15 (e.g., the electrical potential or other physical characteristics associated with nerve bundle 40), control circuit 16 may receive the measured information, determine the status of the nerve bundle 40, and/or compute one or more pulse parameters used to stimulate the nerve bundle. In some aspects, for instance, control circuit 16 may be configured to determine the timing, duration, amplitude, direction etc., of the electrical pulse(s) required for stimulating the nerve bundle 40 at a future time based on the electrical potentials and/or other parameters of the nerve bundle. In this example, control circuit 16 may then apply a control signal to the electrode array 18 and/or capacitive storage element or other chargeable storage element 14 to emit electrical pulses in accordance with the determined pulse parameters using energy stored within the capacitive storage.

Figure 5:
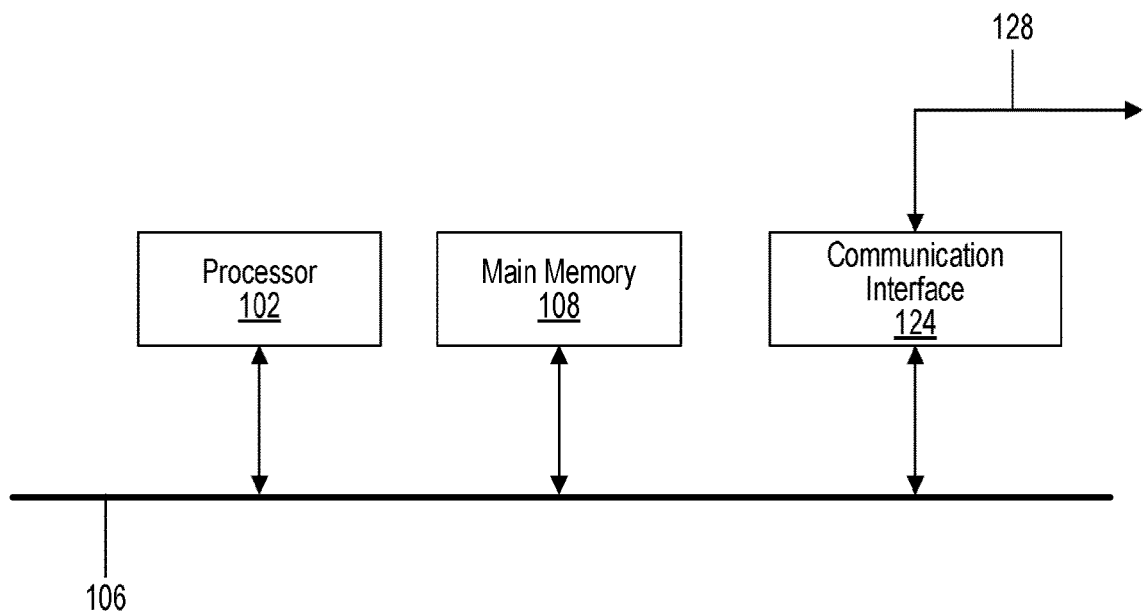
FIG. 5 depicts example computing components, consistent with the disclosed embodiments.

FIG. 5 depicts example computing components 100, consistent with the disclosed embodiments. In some aspects, computing components 100 may comprise computerized programs, modules, and/or code associated with a control circuit (e.g., control circuit 16, a control circuit implemented within wireless transmitter 30, etc.) performing one or more functions or processes disclosed herein. Computing components 100 may also be used to implement one or more of the other components shown in FIG. 1.

In some embodiments, computing components 100 may include one or more microprocessors or processors 102 connected to a communications backbone 106 such as a bus or external communications network (e.g., any medium of digital data communication such as a wired or wireless network and any associated protocols). Communications backbone 106 and/or one or more other components of computing components 100 may directly or indirectly communicatively connect devices or components with each other, such as sensors 15, electrode array 18, antenna circuit 12, capacitive storage element or other chargeable storage element 14, etc., to control circuit 16 of implantable device 10. Similar types of connections are possible for the components of wireless transmitter 30.

In certain aspects, computing components 100 may include main memory 108. Main memory 108 may comprise random access memory (RAM), flash memory, etc., representing a tangible and nontransitory computer-readable medium storing computer programs, modules, sets of instructions, code, and/or data executed with processor 102. When executed by processor 102, such computer programs, modules, code, etc., enable processor 102 to perform one or more processes or functions consistent with the disclosed embodiments. In some aspects, machine code (e.g., from a compiler) and/or files containing code that processor 102 may be executed with an interpreter.

In some aspects, main memory 108 may also include or connect to a secondary memory (not pictured). The secondary memory may include a drive (e.g., HOD, SSD), and/or a removable storage drive 214, such as a magnetic tape drive, flash memory, or the like. The removable storage drive 214 may read from and/or write to a removable storage unit. The removable storage unit may represent a magnetic tape, optical disk, or other storage medium that is read by and written to by the removable storage drive. The removable storage unit may represent a tangible and non-transitory computer-readable medium having stored therein computer programs, sets of instructions, code, and/or data to be executed by processor 102.

In other embodiments, the secondary memory may include other structure or means for allowing computer programs, modules, or instructions to be loaded into computer components 100. Such means may include, for example, a removable storage unit or an interface. Additional examples include a removable memory chip (e.g., EPROM, RAM, ROM, DRAM, EEPROM, flash memory devices, or other volatile or nonvolatile memory devices) and associated socket, or other removable storage units and interfaces, which allow programs, modules, instructions and data to be transferred from the removable storage unit to computing components 100.

Computing components 100 may also include one or more communications interfaces 124. Communications interface 124 may allow computer programs, modules, instructions, and data to be transferred between the computing components 100 and external systems (e.g., in addition to backbone 106). Communications interface 124 may include a modem, a network interface (e.g., an Ethernet card), a communications port, a PCMCIA slot and card, etc. Communications interface 124 may transfer computer programs, modules, instructions, and data in the form of signals, which may be electronic, electromagnetic, optical or other signals capable of being received by communications interface 124. These signals may be provided to communications interface 124 via a communications patt1 (e.g., channel 128). Channel 128 may carry signals and may be implemented using wire, cable, fiber optics, RF link, and/or other communications channels. In one embodiment, the signals comprise data packets sent to or coming from processor 102. For example, computer components 100 may receive signals from a set of sensors (e.g., sensors 15) via communications interface 124, communications backbone 106, or coupling such as interconnection 19. Information representing processed packets may also be sent in the form of signals from processor 102 through communications path 128.

In certain aspects, the computer-implemented operations and methods described herein may be implemented on a single processor, such as processor 102 of computing components 100. In other embodiments, these computer-implemented operations and methods may be implemented using one or more processors within a single computing system and/or on one or more processors within separate computing systems in communication over a network.

In certain embodiments, the terms "storage device" and "storage medium" may refer to particular devices including, but not limited to, main memory 108, secondary memory, a hard disk installed in hard disk drive, and a removable storage unit. Further, the term "computer-readable medium" may refer to devices including, but not limited to, a hard disk installed in hard a disk drive, any combination of main memory 108 and a secondary memory, and removable storage unit, which may respectively provide computer programs and/or sets of instructions to processor 102 of computing components 100. Such computer programs and sets of instructions can be stored within one or more computer-readable media. In certain aspects, computer programs and sets of instructions may also be received via communications interface 124 and stored on the one or more computer-readable media.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components of implantable device 10 and wireless transmitter 30 have be described as being coupled to other components in particular, any such components of these devices may be coupled together.

Computer programs, program modules, and code based on the written description of this specification, such as those used by the control circuit, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

The invention claimed is:

1. A system for stimulating a one or more nerves with an implantable device, the implantable device comprising:
   an antenna circuit tunable to a working frequency, the antenna circuit comprising an antenna and configured to detect a modulated data signal received by the antenna;
   a control circuit coupled to the antenna circuit, the control circuit comprising a rectifying diode configured to rectify an alternating voltage induced in the antenna circuit by an external electromagnetic field and a demodulation circuit that is configured to extract the modulated data signal and to one or more of process and interpret data from the modulated data signal;
   a chargeable storage element, coupled to the control circuit, configured to store energy from the rectified voltage;
   an electrode array coupled to the control circuit and the chargeable storage element, the electrode array comprising a set of electrodes and configured to emit an electric field for stimulating the one or more nerves using the stored energy in response to a control signal emitted from the control circuit;
   a plurality of sensors coupled to the control circuit and configured to measure an electrical potential associated with the one or more nerves after stimulation, wherein the modulated data signal includes pulse parameters for the electric field based on the measured electrical potential; and
   a soft polymer substrate configured to support the antenna circuit, the control circuit, the chargeable storage element, and the electrode array and configured to form a cuff.

2. The system of claim 1, further comprising a wireless transmitter configured to generate the external electromagnetic field.

3. The system of claim 2, wherein the wireless transmitter is embedded in an object external to the implantable device.

4. The system of claim 2, wherein the wireless transmitter comprises an antenna array comprising a plurality of antennas configured to emit the external electromagnetic field.

5. The system of claim 4, wherein at least two antennas of the plurality of antennas have different orientations.

6. The system of claim 1, further comprises a plurality of sensors coupled to the control circuit, the plurality of sensors configured to detect an electrical potential within the cuff.

7. The system of claim 6, wherein:
   the antenna circuit comprises at least one input terminal; and the control circuit is configured to:
   apply an excitation signal to the input terminal, causing the antenna circuit to generate a second electromagnetic field oscillating at the working frequency; and
   modulate the amplitude of the excitation signal based on a measured electrical potential from the plurality of sensors to form a second modulated data signal.

8. The system of claim 7, further comprising a wireless transmitter configured to generate the external electromagnetic field, wherein the wireless transmitter comprises a second demodulation circuit that is configured to demodulate the second modulated data signal formed in the antenna circuit by the modulated excitation signal.

9. The system of claim 8, wherein data from the second modulated data signal includes a status of the nerve bundle based on the electrical potential detected by the plurality of sensors.

10. The system of claim 9, wherein the data in the modulated data signal is based on the status of the nerve bundle.

11. The system of claim 1, wherein the substrate further comprises a rectangular neck section on which the control circuit is affixed and a circular head section on which the antenna is affixed.

12. The system of claim 11, wherein the chargeable storage element comprises a capacitive storage element affixed to the circular head section within the antenna circuit, and wherein the implantable device further comprises a plurality of sensors embedded onto the substrate for detecting electrical potentials.

13. The system of claim 11, wherein the substrate further comprises at least two peripheral tabs includes a first linkable peripheral tab on an edge adjacent to the neck section and a second linkable peripheral tab on an edge opposite the neck section.

14. The system of claim 11, wherein the chargeable storage element is affixed to the neck section.

15. The system of claim 1, wherein the chargeable storage element comprises a capacitive storage element.

16. The system of claim 15, wherein the capacitive storage element has a capacitance of less than 1 nF, preferably less than 75 pF.

17. The system of claim 15, wherein the control circuit and the capacitive storage element are incorporated on an integrated circuit.

18. The system of claim 15, wherein the capacitive storage element is external to the control circuit.

19. The system of claim 1, wherein the electrode array comprises a plurality of electrodes coupled via a high-density, flexible interconnection made of a metal.

20. The system of claim 1, wherein the control circuit is configured to apply the control signal at a predetermined time to stimulate one or more nerves in proximity to the implantable device.

21. The system of claim 1, wherein the electrode array is configured to emit the electric field in a plurality of pulses to stimulate the one or more nerves, wherein the plurality of pulses extends for a fixed duration of time.

22. The system of claim 21, wherein the fixed duration of time is between one and five minutes.

23. A method for stimulating a nerve bundle with an implantable device, the implantable device comprising an antenna circuit including one or more input terminals, a control circuit coupled to the antenna circuit, a chargeable storage element coupled to the control circuit, an electrode array coupled to the control circuit and capacitive storage, and a plurality of sensors coupled to the control circuit, the method comprising:

after implantation of the implantable device, rectifying a voltage induced in the antenna circuit from an external electromagnetic field with a rectifying diode in the control circuit;

detecting a modulated data signal received by the antenna circuit;

demodulating the modulated data signal to process a plurality of pulse parameters interpreted from the modulated data signal;

storing the rectified voltage as energy in the chargeable storage element;

applying a control signal from the control circuit to an electrode terminal of the electrode array in accordance with the plurality of pulse parameters;

emitting an electrical pulse from the electrode array using the stored energy to stimulate the nerve bundle, the electrical pulse based on the control signal and the plurality of pulse parameters;

measuring, with the plurality of sensors, an electrical potential associated with the nerve bundle after stimulation; and applying a modulated excitation signal from the control circuit to an input terminal of the antenna circuit, the excitation signal modulated based on the measured electrical potential.

24. The method of claim 23, wherein the data of the modulated signal includes pulse parameters for the electrical pulse.

25. A method for stimulating a nerve bundle with an implantable device, the implantable device comprising an antenna circuit including one or more input terminals, a control circuit coupled to the antenna circuit, a chargeable storage element coupled to the control circuit, an electrode array coupled to the control circuit and the chargeable storage element, and a plurality of sensors coupled to the control circuit, the method comprising:

measuring, with the plurality of sensors, an electrical potential associated with the nerve bundle after implantation of the implantable device;

applying a modulated excitation signal from the control circuit to an input terminal of the antenna circuit, the excitation signal modulated based on the measured electrical potential;

demodulating a data signal formed in the antenna array from a first external electromagnetic field emitted from a wireless transmitter, the data signal including a plurality of pulse parameters indicative of characteristics of an electrical pulse;

applying a control signal to an electrode terminal of the electrode array, the control signal based on the plurality of pulse parameters; and emitting an electrical pulse from the electrode array in accordance with the plurality of pulse parameters to stimulate the nerve bundle, the electrical pulse generated from energy stored in the chargeable storage element, wherein the plurality of pulse parameters is based on the measured electrical potential.

\* \* \* \* \*